United States Patent
Uehara et al.

(10) Patent No.: US 11,445,931 B2
(45) Date of Patent: Sep. 20, 2022

(54) OPERATION PROCESSING APPARATUS CALCULATING NUMERICAL VALUE REPRESENTING SKIN BARRIER FUNCTION, EQUIPMENT, COMPUTER READABLE MEDIUM, AND METHOD FOR EVALUATING SKIN BARRIER FUNCTION

(71) Applicant: ALCARE CO., LTD., Tokyo (JP)

(72) Inventors: Osamu Uehara, Tokyo (JP); Kenichi Matsuzaki, Tokyo (JP); Takao Nakamura, Kayama (JP); Toshimasa Kusuhara, Okayama (JP)

(73) Assignee: ALCARE CO., LTD., Tokyo (JP)

( * ) Notice: Subject to any disclaimer, the term of this patent is extended or adjusted under 35 U.S.C. 154(b) by 266 days.

(21) Appl. No.: 16/663,218

(22) Filed: Oct. 24, 2019

(65) Prior Publication Data
US 2020/0054237 A1    Feb. 20, 2020

Related U.S. Application Data

(62) Division of application No. 15/296,385, filed on Oct. 18, 2016, now abandoned.

(51) Int. Cl.
*A61B 5/053* (2021.01)
*A61B 5/00* (2006.01)
*A61B 5/0531* (2021.01)

(52) U.S. Cl.
CPC ............ *A61B 5/0531* (2013.01); *A61B 5/441* (2013.01)

(58) Field of Classification Search
None
See application file for complete search history.

(56) References Cited

U.S. PATENT DOCUMENTS

| | | | | |
|---|---|---|---|---|
| 5,086,781 A * | 2/1992 | Bookspan | ............ | A61B 5/4869 600/547 |
| 5,738,107 A * | 4/1998 | Martinsen | ............... | A61B 5/442 600/547 |
| 7,753,846 B2 * | 7/2010 | Park | ..................... | A61B 5/0531 600/307 |
| 8,273,021 B2 * | 9/2012 | Jang | ..................... | A61B 5/0531 600/307 |

(Continued)

FOREIGN PATENT DOCUMENTS

JP    2010172543 A  *  8/2010

OTHER PUBLICATIONS

JP2010172543A Machine Translation (Year: 2010).*

*Primary Examiner* — Sean P Dougherty
*Assistant Examiner* — Benjamin S Melhus
(74) *Attorney, Agent, or Firm* — IP Business Solutions, LLC

(57) ABSTRACT

The goal of the present invention is to calculate with high accuracy a numerical value representing skin barrier function in a wide range of skin conditions. Provided is an operation processing apparatus calculates a first variable based on delay time measured using an alternating-current (AC) signal generated by the AC signal generation circuit and a signal applied by an application electrode and passing through skin and stores the first variable calculated by the processor as a calculation result. The operation processing apparatus calculates a numerical value representing the skin barrier function based on the calculation result.

2 Claims, 10 Drawing Sheets

(56) References Cited

U.S. PATENT DOCUMENTS

| | | | |
|---|---|---|---|
| 9,002,444 B2 * | 4/2015 | Jang | A61B 5/442 600/547 |
| 2003/0216661 A1 * | 11/2003 | Davies | A61B 5/0538 600/547 |
| 2006/0100532 A1 * | 5/2006 | Bae | A61B 5/0537 600/506 |
| 2007/0043301 A1 * | 2/2007 | Martinsen | A61B 5/0531 600/547 |
| 2008/0012582 A1 * | 1/2008 | Jang | A61B 5/442 324/692 |
| 2008/0033315 A1 * | 2/2008 | Kim | A61B 5/442 600/547 |
| 2008/0045816 A1 * | 2/2008 | Jang | A61B 5/0531 324/692 |
| 2008/0051643 A1 * | 2/2008 | Park | A61B 5/0531 600/306 |
| 2008/0091091 A1 * | 4/2008 | Jang | A61B 5/442 600/306 |
| 2009/0264792 A1 * | 10/2009 | Mazar | A61B 5/259 600/547 |
| 2010/0179403 A1 * | 7/2010 | Martinsen | A61B 5/4266 600/346 |
| 2011/0060241 A1 * | 3/2011 | Martinsen | A61B 5/6838 600/547 |
| 2011/0301441 A1 * | 12/2011 | Bandic | A61B 5/4875 600/306 |
| 2012/0232421 A1 * | 9/2012 | Jang | A61B 5/0531 600/547 |
| 2012/0277619 A1 * | 11/2012 | Starkebaum | A23L 33/30 600/547 |
| 2013/0078209 A1 * | 3/2013 | Yu | A61K 31/80 424/78.05 |
| 2015/0073252 A1 * | 3/2015 | Mazar | A61B 5/0205 600/391 |
| 2015/0245785 A1 * | 9/2015 | Slizynski | A61B 5/4869 600/547 |
| 2016/0128605 A1 * | 5/2016 | Moreno | A23L 33/30 600/547 |
| 2017/0007186 A1 * | 1/2017 | Baek | A61B 5/0535 |
| 2017/0296090 A1 * | 10/2017 | Kalvøy | A61B 5/0537 |

* cited by examiner

[Fig. 1]
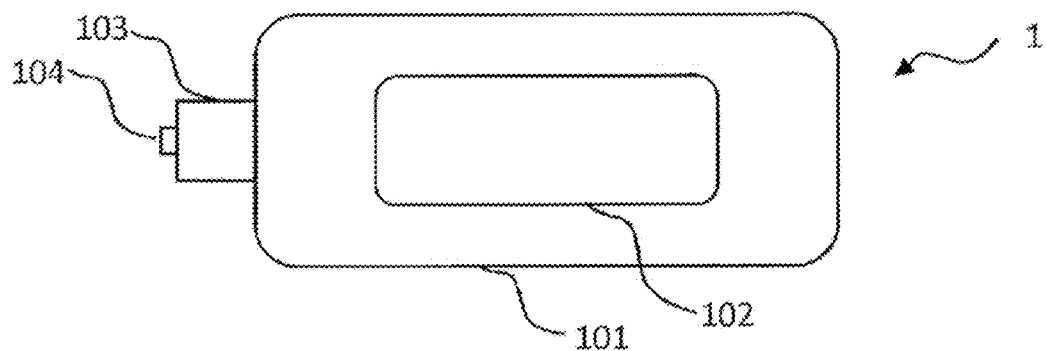
[Fig. 2]
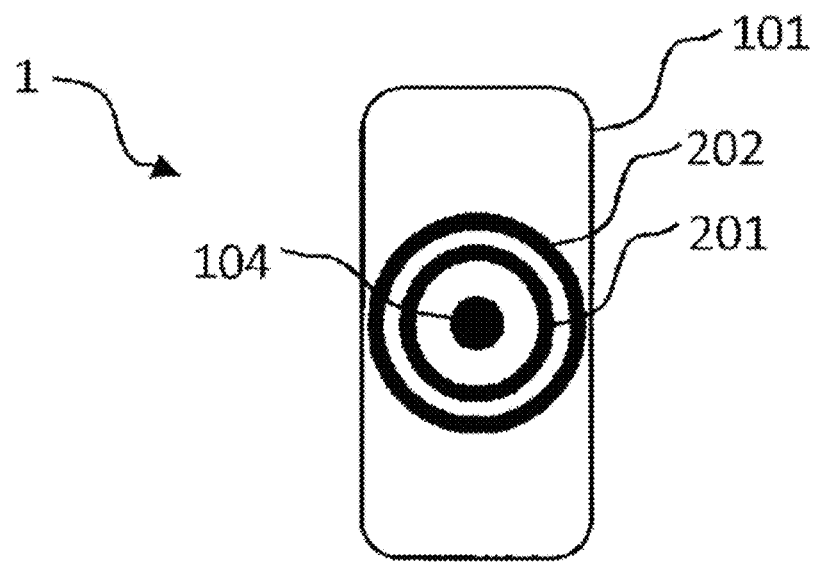

[Fig. 3]
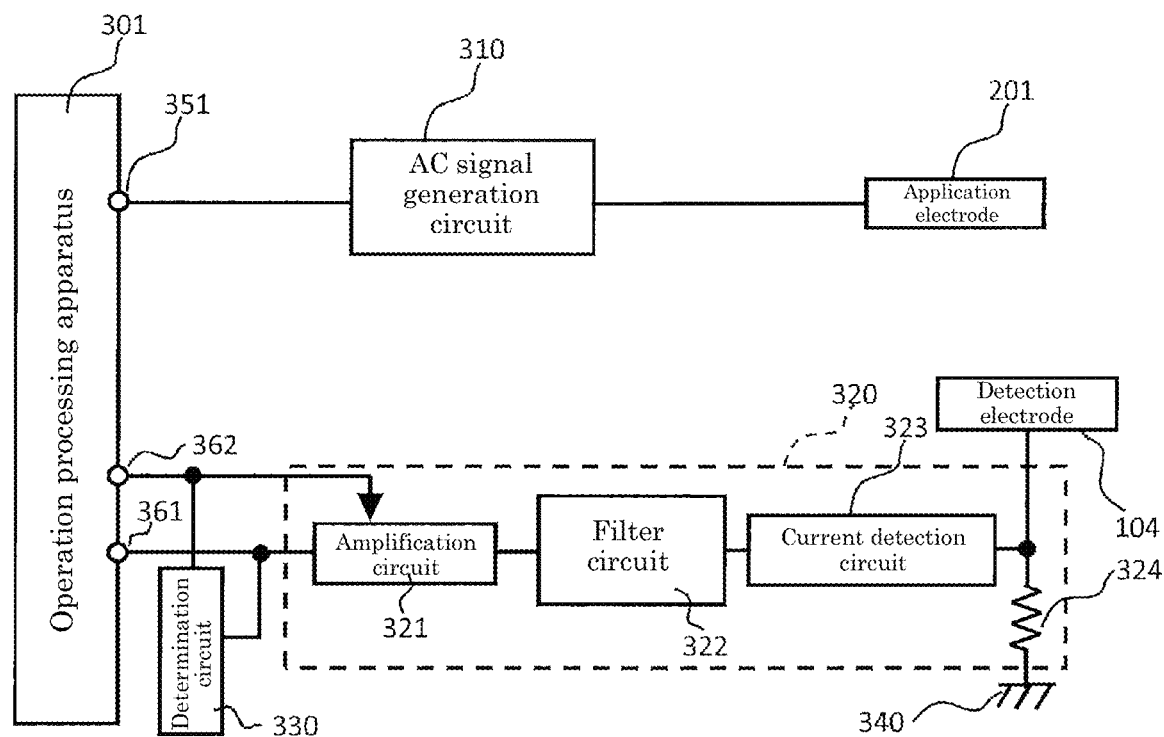

[Fig. 4]
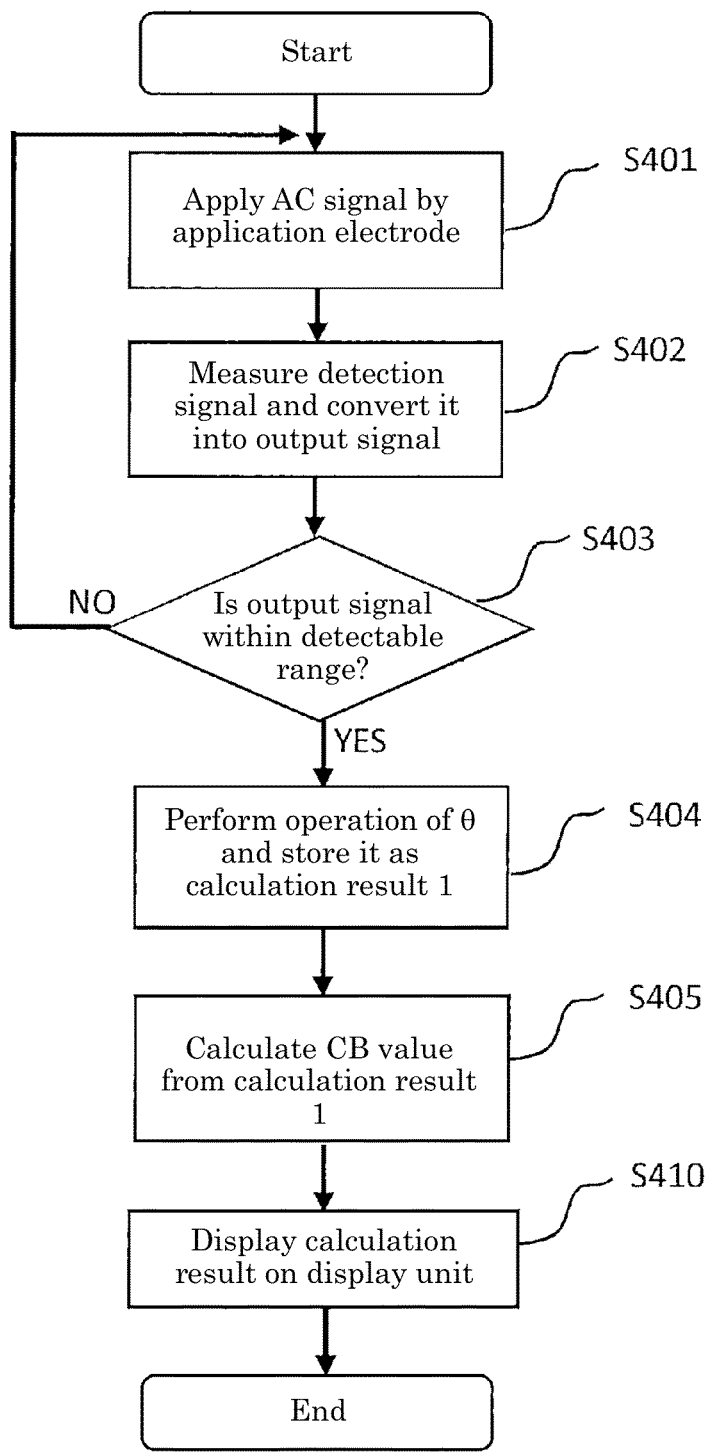

[Fig. 5]
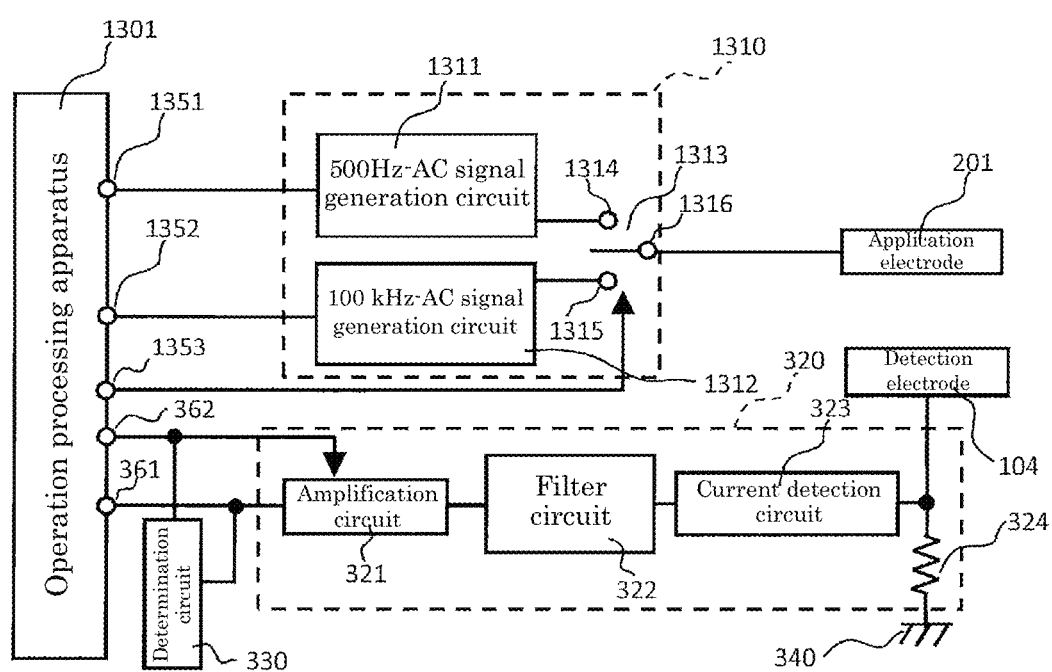

[Fig. 6]
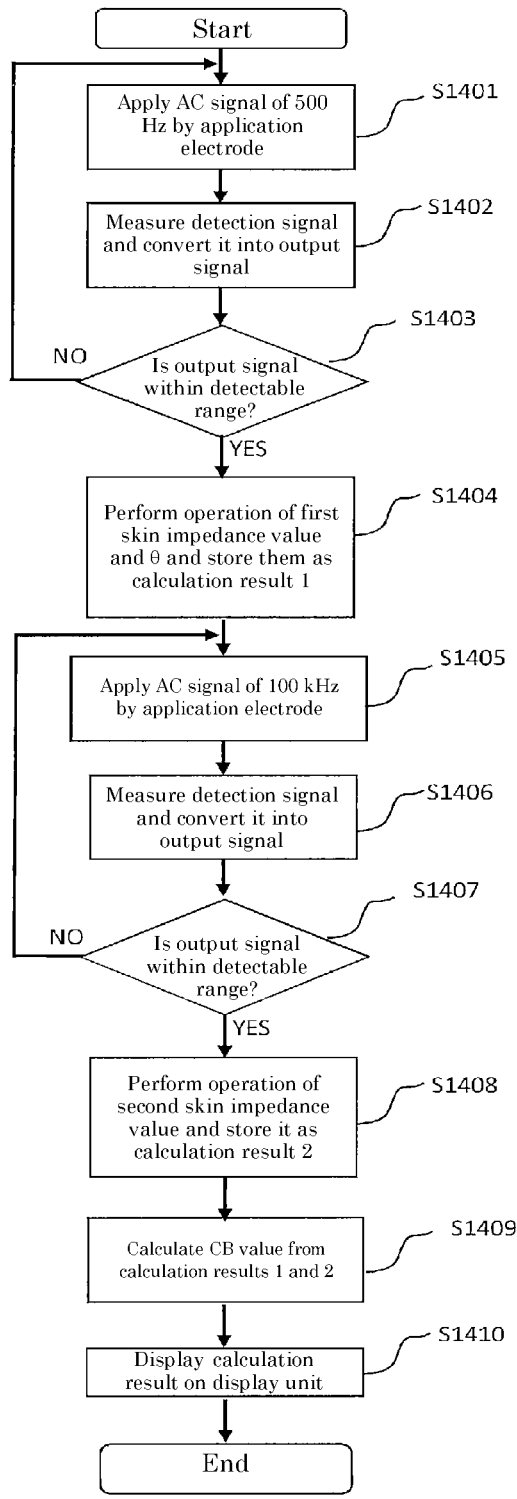

[Fig. 7]
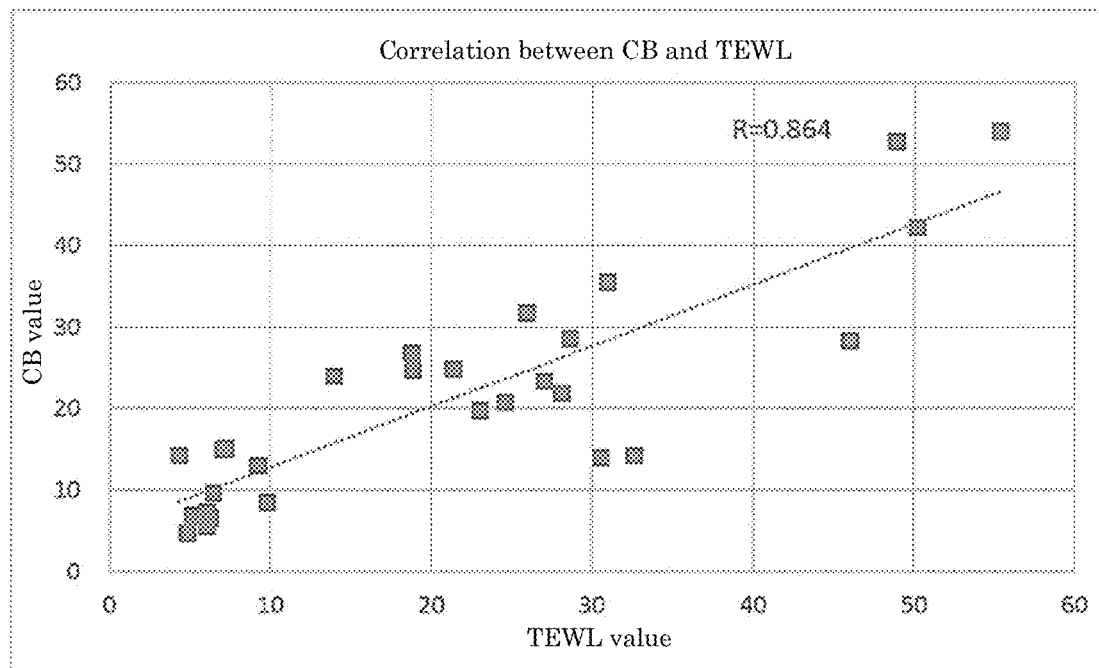

[Fig. 8]
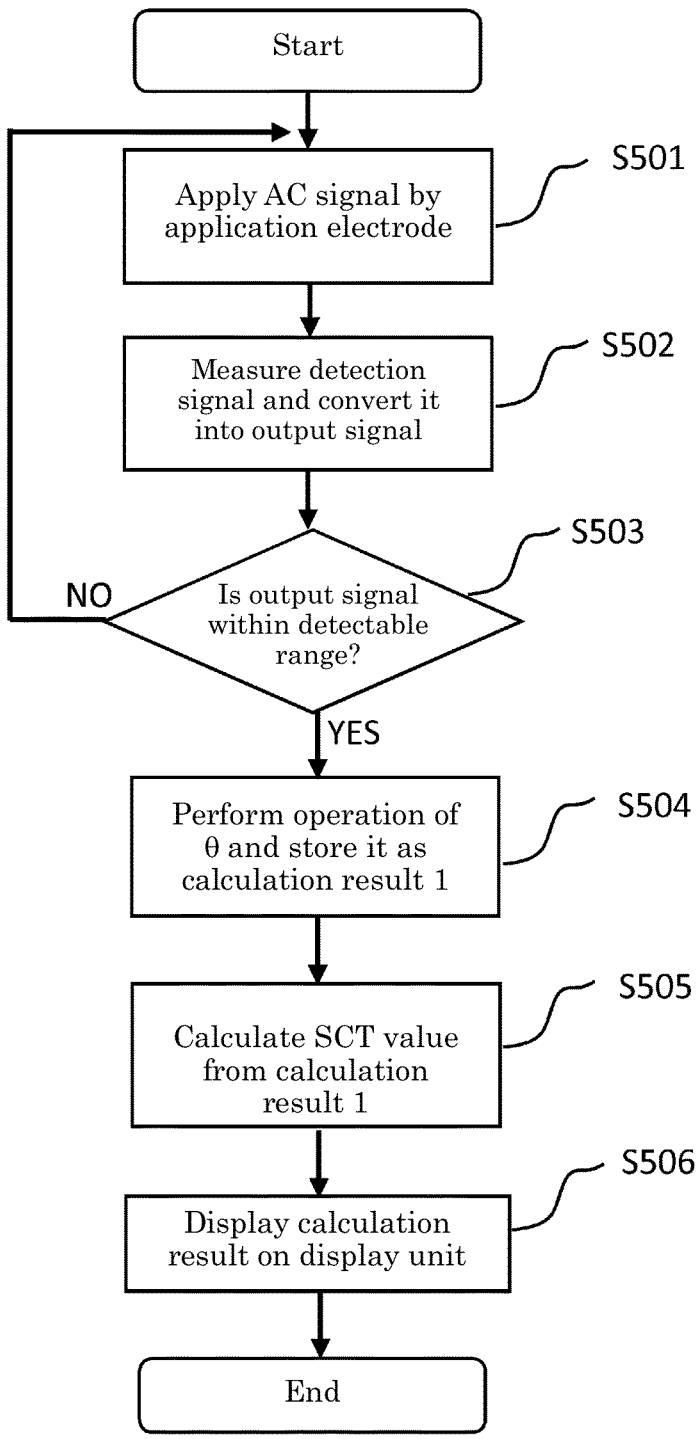

[Fig. 9]
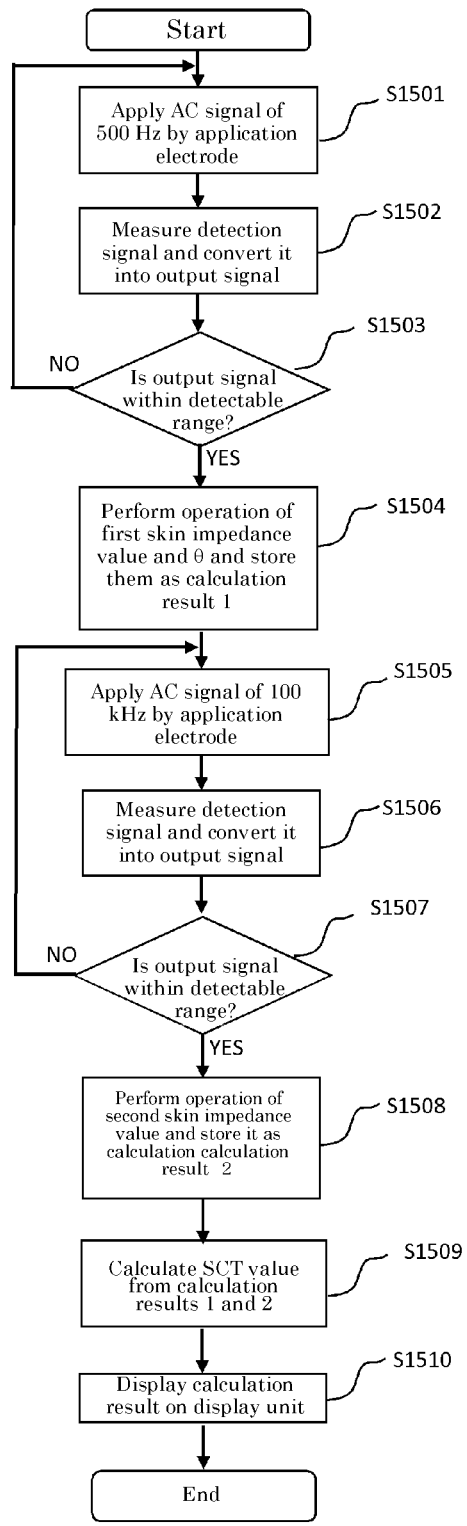

[Fig. 10]
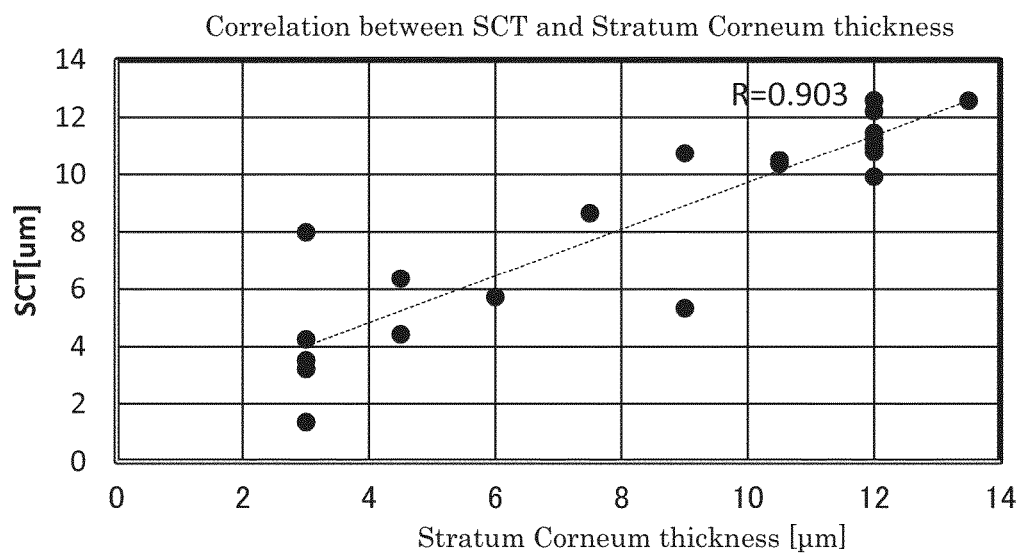
[Fig. 11]
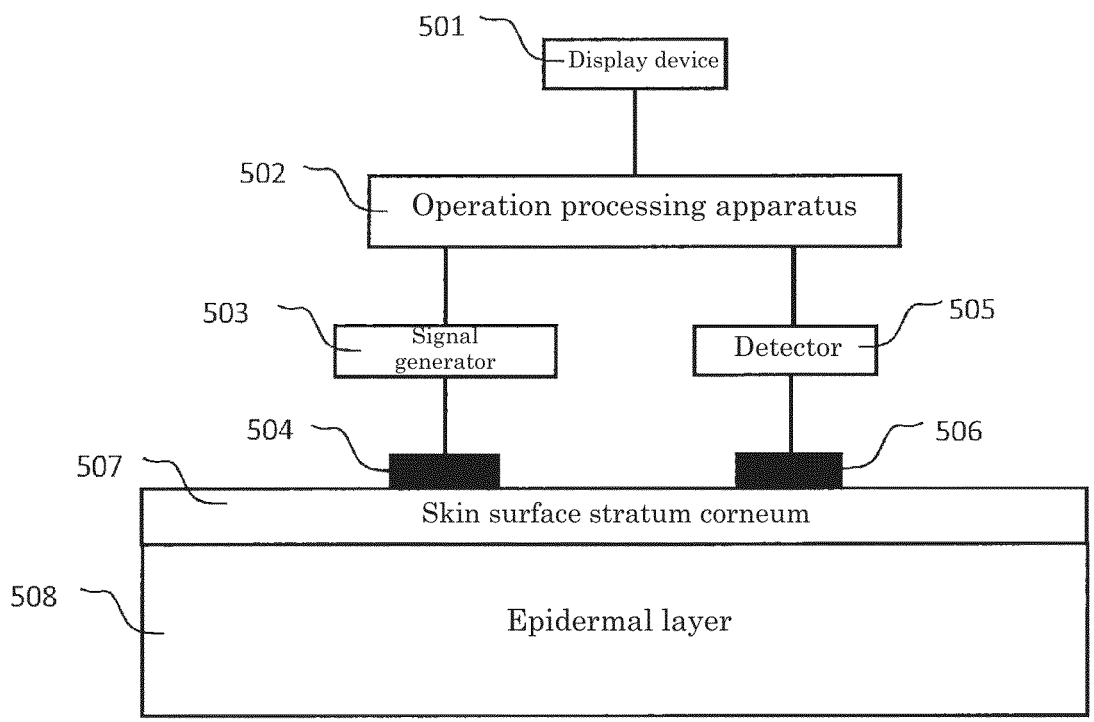
PRIOR ART

[Fig. 12]
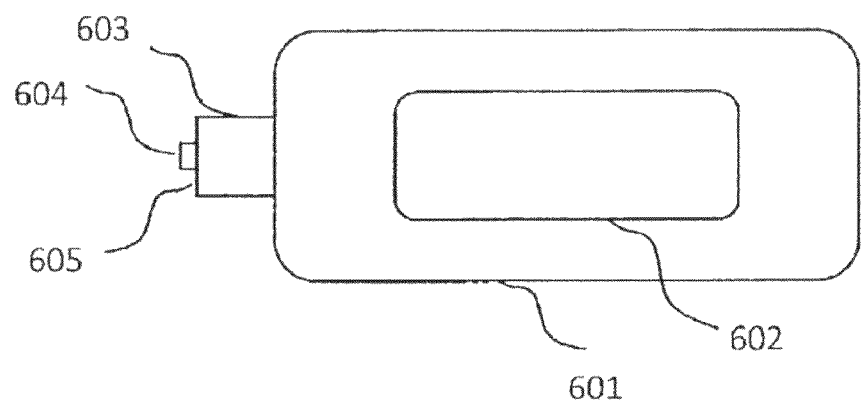
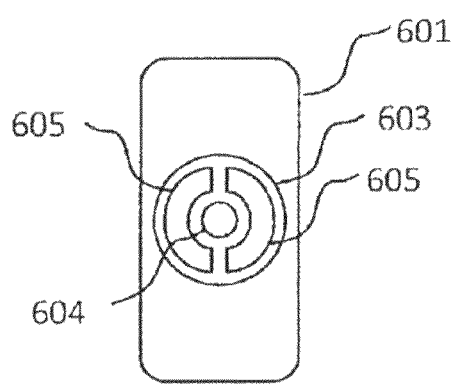
PRIOR ART

US 11,445,931 B2

OPERATION PROCESSING APPARATUS CALCULATING NUMERICAL VALUE REPRESENTING SKIN BARRIER FUNCTION, EQUIPMENT, COMPUTER READABLE MEDIUM, AND METHOD FOR EVALUATING SKIN BARRIER FUNCTION

CROSS-REFERENCE TO RELATED APPLICATIONS

This is a divisional application claiming priority to U.S. patent application Ser. No. 15/296,385 which is incorporated herein by reference.

BACKGROUND OF THE INVENTION

1. Field of the Invention

The present invention relates to an operation processing apparatus calculating a numerical value representing a skin barrier function, equipment, a computer readable medium, and a method for evaluating the skin barrier function, and in particular, to the operation processing apparatus and the like for accurately calculating a numerical value representing the skin barrier function in a wide range of skin conditions.

2. Description of Related Art

FIG. 11 is a block diagram illustrating a skin barrier function measurement circuit including a conventional operation processing apparatus. The skin barrier function measurement circuit described in FIG. 11 has a display device 501, an operation processing apparatus 502, a signal generator 503, a detector 505, an application electrode 504, and a detection electrode 506.

After the application electrode 504 and the detection electrode 506 are made contact with skin, an alternating-current (AC) signal generated by the signal generator 503 is applied to the skin by the application electrode 504. After the AC signal passes through a skin surface stratum corneum 507 and an epidermal layer 508 in the skin, the AC signal is detected by the detector 505 through the detection electrode 506. The operation processing apparatus 502 performs operation processing on the detected signal to calculate a characteristic value that can be of the stratum corneum barrier function, and displays it on the display device 501.

FIG. 12 is an equipment diagram illustrating electronic equipment including the conventional operation processing apparatus. The electronic equipment has a main body 601 which has the operation processing apparatus, a display unit 602, a probe 603, a detection electrode 604, and an application electrode 605.

An electric signal generated by the application electrode 605 passes through skin and the passed signal is detected through the detection electrode 604. The operation processing apparatus performs specified operation processing on the detected electric signal to calculate a susceptance value, an admittance value and the like. A characteristic value corresponding to the stratum corneum barrier function is calculated based on these values. The characteristic value is displayed on the display unit 602.

However, in the field of the invention, the electronic equipment including the conventional operation processing apparatus is required to accurately calculate a numerical value representing a skin barrier function in a wide range of skin conditions from a normal condition to a rough skin condition, in which a stratum corneum is totally exfoliated, or the like.

SUMMARY OF THE INVENTION

The present invention is directed to an operation processing apparatus which can accurately calculate a numerical value representing a skin barrier function in a wide range of skin conditions, electronic equipment, a computer readable storage medium and an evaluation method of the skin barrier function.

To achieve the above object, an operation processing apparatus calculates a numerical value representing a skin barrier function based on a first variable based on delay time measured using an alternating-current (AC) signal generated by an AC signal generation circuit and a signal applied by an application electrode and passing through skin.

The operation processing apparatus in the present invention can accurately calculate a numerical value representing a skin barrier function in a wide range of skin conditions.

BRIEF DESCRIPTION OF THE DRAWINGS

FIG. 1 is an equipment diagram illustrating electronic equipment including an operation processing apparatus according to the first embodiment of the present invention;

FIG. 2 is an equipment diagram illustrating a probe of the electronic equipment shown in FIG. 1;

FIG. 3 is a circuit diagram illustrating a skin barrier function measurement circuit included in the electronic equipment according to the first embodiment of the present invention;

FIG. 4 is a flowchart illustrating operations of the skin barrier function measurement circuit shown in FIG. 3;

FIG. 5 is a circuit diagram illustrating a skin barrier function measurement circuit of electronic equipment including an operation processing apparatus according to the second embodiment of the present invention;

FIG. 6 is a flowchart illustrating operations of the skin barrier function measurement circuit shown in FIG. 5;

FIG. 7 is a chart illustrating a correlation of a numerical value (CB value) representing a skin barrier function and a numerical value measured by a transepidermal water loss method;

FIG. 8 is a flowchart illustrating operations of a skin barrier function measurement circuit of electronic equipment including an operation processing apparatus according to the third embodiment of the present invention;

FIG. 9 is a flowchart illustrating operations of a skin barrier function measurement circuit of electronic equipment including an operation processing apparatus according to the fourth embodiment of the present invention;

FIG. 10 is a chart illustrating a correlation of a numerical value (SCT value) representing the skin barrier function and a numerical value measured by the transepidermal water loss method;

FIG. 11 is a block diagram illustrating a skin barrier function measurement circuit including the conventional operation processing apparatus; and FIG. 12 is an equipment diagram illustrating electronic equipment including the conventional operation processing apparatus.

DESCRIPTION OF THE EMBODIMENTS

The preferred embodiments of the present invention are described below with reference to the drawings. The embodiments are mere examples for the representative embodiments of the invention, and they do not by any means limit the technical scope of the invention.

FIG. 1 is an equipment diagram illustrating electronic equipment including an operation processing apparatus according to the first embodiment of the invention. The electronic equipment 1 includes a main body portion 101, a display unit 102, a probe 103, and a detection electrode 104. FIG. 2 is an equipment diagram illustrating the configuration of the probe 103. The probe 103 includes the detection electrode 104, an application electrode 201, and a ground electrode 202. The probe 103 is used for evaluating a skin barrier function of human skin. The ground electrode 202 of the probe 103 prevents influence of external noise on the measurement from propagating the detection electrode 104 and the application electrode 201 at the time of the measurement.

Then, operations of the electronic equipment 1 are described.

After a power supply of the main body portion 101 is turned on, the detection electrode 104 and the application electrode 201 are made contact with skin. After a measurement start switch is turned on, a skin barrier function measurement circuit in the main body portion 101 is made to operate. The skin barrier function measurement circuit applies an alternating-current (AC) signal to the skin in which a skin barrier function is evaluated. The operation processing apparatus in the electronic equipment 1 calculates a phase angle (hereinafter, expressed as θ) based on delay time measured using the AC signal and a signal that has passed through the skin detected by the detection electrode 104. The detected signal is called a detection signal. The θ is an example of a first variable of the embodiment. The calculation method of the θ is described later. The operation processing apparatus, which will be described later, calculates a numerical value representing the skin barrier function with the first variable and the numerical value is displayed on the display unit 102.

For example, $\theta=2\pi f\Delta t$, where $\Delta t$ is delay time measured using the AC signal and the detection signal, and f is frequency of the AC, can be satisfied. The θ changes based on the delay time measured using the AC signal and the detection signal (hereinafter, the same holds true for a relation of the delay time measured using the AC signal and the detection signal and θ).

The configuration of the probe 103 is not limited to the configuration of FIG. 2. The configuration of the probe 103 may employ any configuration as long as it can apply an AC signal to human skin and detect a signal that has passed through the skin. The ground electrode 202 is not necessarily used if influence of the external noise on the measurement can be reduced at the time of the measurement. The electronic equipment 1 is not limited to the above-mentioned configuration. The electronic equipment 1 can apply any electronic equipment such as a mobile phone, a smart phone and a watch as long as it has the configuration capable of incorporating therein the probe 103 and the skin barrier function measurement circuit.

FIG. 3 is a circuit diagram illustrating the skin barrier function measurement circuit included in the electronic equipment 1 including the operation processing apparatus according to the first embodiment of the invention. The skin barrier function measurement circuit includes an operation processing apparatus 301, an AC signal generation circuit 310, a signal detection circuit 320, a determination circuit 330, and a ground terminal 340 connected to the ground electrode 202.

The operation processing apparatus 301 includes an output terminal 351 and input terminals 361 and 362. The signal detection circuit 320 includes an amplification circuit 321, a filter circuit 322, a current detection circuit 323, and a detection resistance 324.

Then, connections of the skin barrier function measurement circuit are described. The output terminal 351 of the operation processing apparatus 301 is connected to input of the AC signal generation circuit 310 and output of the AC signal generation circuit 310 is connected to the application electrode 201. The input terminal 361 is connected to output of the amplification circuit 321 and input of the determination circuit 330 and the input terminal 362 is connected to output of the determination circuit 330 and the amplification circuit 321.

The detection electrode 104 is connected to one terminal of the detection resistance 324 and input of the current detection circuit 323. The other terminal of the detection resistance 324 is connected to the ground terminal 340. Output of the current detection circuit 323 is connected to input of the filter circuit 322 and output of the filter circuit 322 is connected to input of the amplification circuit 321.

Referring to FIG. 3 and FIG. 4, operations of the skin barrier function measurement circuit are described. After the probe 103 is pressed against the human skin, the measurement starts.

First, the operation processing apparatus 301 outputs a control signal to cause the AC signal generation circuit 310 to generate an AC signal. The AC signal generation circuit 310 generates an AC signal using the control signal output by the operation processing unit 301. The AC signal generated is applied to the skin by the application electrode 201 (step S401).

The detection electrode 104 detects an AC signal passing through the skin and outputs the detection signal to the signal detection circuit 320. Hereinafter, an AC signal detected by the detection electrode is expressed as the detection signal. The signal detection circuit 320 converts the detection signal into an output signal. The output signal is output by the signal detection circuit 320 to the determination circuit 330 (step S402).

The determination circuit 330 determines whether the output signal falls within the range that the operation processing apparatus 301 can detect (step S403).

If the determination circuit 330 determines that the output signal does not fall within the range that the operation processing apparatus 301 can detect (NO at step S403), the operation processing apparatus 301 changes gain of the amplification circuit 321 in the signal detection circuit 320. Thereafter, the AC signal is applied to the skin by the application electrode 201 again (step S401) and the detection electrode 104 detects a detection signal passing through skin and outputs the detection signal to the signal detection circuit 320. The signal detection circuit 320 converts the detection signal into an output signal again (step S402). These processes are repeated until the output signal falls within the range that the operation processing apparatus 301 can detect.

If the determination circuit 330 determines that the output signal is a value in the detectable range (YES at step S403), the operation processing apparatus 301 calculates θ based on delay time measured using the AC signal and the detection signal. The calculated θ is stored in a storage medium in the operation processing apparatus 301 as a calculation result 1 (step S404).

The processor in the operation processing apparatus 301 calculates a numerical value representing a first skin barrier function (hereinafter, expressed as a CB value) assigning θ stored as the calculation result 1 to the following equation 1 (step S405).

$$CB = a \times \theta + \alpha \quad \text{[Equation 1]}$$

In the equation, a and α are specified constants. The calculation method of the a and α is described later.

The display unit 102 displays the CB value (step S410).

The calculation method of the a and α is described. The specified constants a and α are values that are appropriately defined by the regression analysis.

As described in the method above, θ is calculated with skins of a plurality of persons. Trans epidermal water losses (hereinafter, abbreviated as TEWL in some cases) is measured in the same part of the skin where θ is calculated. TEWL is one parameter of conventional evaluation of the skin barrier function.

The regression analysis is performed on a plurality of sets of θ and the TEWL values obtained in the measure described above to determine the specified constants a and α in the equation 1. These constants are determined so that θ can have a good correlation with TEWL.

It should be noted that the indicator of the skin barrier function is not limited to TEWL, so another indicator may be used as long as it can evaluate the skin barrier function.

As described in the method above, the operation processing apparatus in the first embodiment calculates CB value based on the θ with the processor in the operation processing apparatus 301. The θ and the TEWL values are measured in a wide range of skin conditions from a normal condition skin to a rough condition skin. The equation is determined so that the θ can have a good correlation with the TEWL values. The CB, one parameter of evaluation of the skin barrier function, is a numerical value accurately representing a skin barrier function in a wide range of skin conditions from a normal condition skin to a rough condition skin. The operation processing apparatus in the first embodiment can accurately calculate a numerical value representing a skin barrier function in a wide range of skin conditions from a normal condition skin to a rough skin condition.

In the electronic equipment 1, the determination circuit 330 employs the method in which it determines the output signal and changes the gain of the amplification circuit 321 according to the result of the determination. The AC signal attenuates when it passes through skin. Amplifying too small AC signal leads to much noise, which lacks precision of the detection. On the other hand, too large AC signal falls outside a detectable range. Therefore making the detection signal gradually large with the determination circuit 330 enables the operation processing apparatus to receive an appropriate input signal. However, the method of detecting the output signal is not limited as long as it can accurately detect the output signal. For example, the determination circuit 330 may employ a method to modify a peak value of the AC signal to maintain the output signal, to which the detection signal is converted, within the detectable range even if the AC signal attenuates after passing through skin. Alternatively, the determination circuit 330 may employ a method to maintain, even if the AC signal attenuates after passing through skin, the output signal within the detectable range, modifying a resistance value of the detection signal to enlarge the peak value of the detection signal.

Furthermore, the AC signal generation circuit may be configured to generate one or more AC signals. If the AC signal generation circuit is configured to generate two or more AC signals, each θ based on the delay time measured using the respective AC signals and the respective detection signals detected based on the AC signals may be calculated. The CB value may be calculated with the θ.

FIG. 5 is a circuit diagram illustrating the skin barrier function measurement circuit including an operation processing apparatus according to the second embodiment of the invention. The skin barrier function measurement circuit in FIG. 5 is different from that of the circuit in FIG. 3 in that an AC signal generation circuit 310 is replaced by the AC signal generation circuit 1310 and the operation processing apparatus 301 is replaced by an operation processing apparatus 1301. On the other hand, other configurations are the same as the respective configurations illustrated in FIG. 1 to FIG. 3, and the same reference numerals denote them and therefore description thereof is omitted.

The operation processing apparatus 1301 includes output terminals 1351, 1352, and 1353.

The AC signal generation circuit 1310 includes a 500 Hz-AC signal generation circuit 1311, a 100 kHz-AC signal generation circuit 1312, and a switching circuit 1313. The switching circuit 1313 includes input terminals 1314 and 1315 and an output terminal 1316.

Connections of the skin barrier function measurement circuit are described.

The output terminal 1351 of the operation processing apparatus 1301 is connected to input of the 500 Hz-AC signal generation circuit 1311, the output terminal 1352 is connected to an input of the 100 kHz-AC signal generation circuit 1312, and the output terminal 1353 is connected to the switching circuit 1313.

Output of the 500 Hz-AC signal generation circuit 1311 is connected to the input terminal 1314 of the switching circuit 1313 and output of the 100 kHz-AC signal generation circuit 1312 is connected to the input terminal 1315 of the switching circuit 1313. The output terminal 1316 of the switching circuit 1313 is connected to the application electrode 201.

Referring to FIG. 5 and FIG. 6, operations of a skin barrier function measurement circuit including the operation processing apparatus 1301 in the second embodiment are described. After the same operation in the first embodiment, the measurement starts.

First, the operation processing apparatus 1301 outputs a control signal to cause the AC signal generation circuit 1310 to generate an AC signal of 500 Hz. The AC signal generation circuit 1310 generates an AC signal of 500 Hz using the control signal output by the operation processing unit 1301. The AC signal of 500 Hz is applied to skin by the application electrode 201 (step S1401).

The detection electrode 104 detects an AC signal passing through the skin and outputs the detection signal to the signal detection circuit 320. The signal detection circuit 320 converts the detection signal into an output signal. The output signal is output by the signal detection circuit 320 to the determination circuit 330 (step S1402).

The determination circuit 330 determines whether the output signal falls within the range that the operation processing apparatus 1301 can detect (step S1403).

If the determination circuit 330 determines that the output signal does not fall within the range that the operation processing apparatus 1301 (NO at step S1403), the operation processing apparatus 1301 changes gain of the amplification circuit 321 in the signal detection circuit 320. Thereafter, the AC signal of 500 Hz is applied to the skin by the application electrode 201 again (step S1401) and the detection electrode 104 detects a detection signal passing through skin and outputs the detection signal to the signal detection circuit 320. The signal detection circuit 320 converts the detection signal into an output signal again (step S1402).These processes are repeated until the output signal falls within the range that the operation processing apparatus 1301 can detect.

If the determination circuit 330 determines that the output signal is a value in the detectable range (YES at step S1403), the operation processing apparatus 1301 calculates θ based on delay time measured using the AC signal of 500 Hz and the detection signal. In addition, the operation processing apparatus 1301 calculates a susceptance value (hereinafter, also expressed as B) based on the θ and a peak value of the detection signal. The B is an example of a first skin impedance of the second embodiments. The calculated θ and B are stored as a calculation result 1 in a storage medium in the operation processing apparatus 1301 (step S1404).

Subsequently, the operation processing apparatus 1301 outputs a control signal to cause the AC signal generation circuit 1310 to generate an AC signal of 100 kHz. The AC signal generation circuit 1310 generates an AC signal of 100 kHz using the control signal output by the operation processing unit 1301. The AC signal of 100 kHz is applied to the skin by the application electrode 201 (step S1405).

The detection electrode 104 detects an AC signal passing through the skin and outputs the detection signal to the signal detection circuit 320. The signal detection circuit 320 converts the detection signal into an output signal. The output signal is output by the signal detection circuit 320 to the determination circuit 330 (step S1406).

The determination circuit 330 determines whether the output signal falls within the range that the operation processing apparatus 1301 can detect (step S1407).

If the determination circuit 330 determines that the output signal does not fall within the range that the operation processing apparatus 1301 can detect (NO at step S1407), the operation processing apparatus 1301 changes gain of the amplification circuit 321 in the signal detection circuit 320. Thereafter, the AC signal of 100 Hz is applied to the skin by the application electrode 201 again (step S1405) and the detection electrode 104 detects a detection signal passing through skin and outputs the detection signal to the signal detection circuit 320. The signal detection circuit 320 converts the detection signal into an output signal again (step S1406). These processes are repeated until the output signal falls within the range that the operation processing apparatus 1301 can detect.

If the determination circuit 330 determines that the output signal is a value in the detectable range (YES at step S1407), the operation processing apparatus 1301 calculates an admittance value (hereinafter, also expressed as Y) based on delay time measured using the AC signal of 100 kHz and the detection signal and a peak value of the detection signal. The Y is an example of a second skin impedance of the second embodiments. The calculated Y is stored as a calculation result 2 in the storage medium in the operation processing apparatus 1301 (step S1408).

The processor in the operation processing apparatus 1301 calculates a numerical value representing a first skin barrier function (CB value) assigning B and θ stored as the calculation result 1 and Y stored as the calculation result 2 to the following equation 2 (step S1409).

$$CB = a1 \times B^o/Y^p + a2 \times \theta + a3 \times Y^k/B^l + a4 \quad \text{[Equation 2]}$$

In the equation, a1, a2, a3, a4, o, p, k, and l are specified constants. The calculation method of the a1, a2, a3, a4, o, p, k, and l is described later.

The display unit 102 displays the CB value calculated based on the equation 2 (step S1410).

The calculation method of the a1, a2, a3, a4, o, p, k, and l is described. The specified constants a1, a2, a3, a4, o, p, k, and 1 are values that are appropriately defined by the regression analysis.

As described in the method above, B, θ, and Y are calculated with skins of a plurality of persons. TEWL is measured in the same part of the skin where B, θ, and Y are calculated. The regression analysis is performed on a plurality of sets of B, θ, and Y and the TEWL values obtained in the measure described above to determine the specified constants a1, a2, a3, a4, o, p, k, and l in the equation 2. These constants are determined so that B, θ, and Y can have a good correlation with TEWL.

For example, numerical values of "14473064" as a1, "−0.39281" as a2, "−1.1E-08" as a3, "49.7361" as a4, "2" as o, "1" as p, "1" as k, and "2" as l are obtained. These values are mere examples of appropriate values. It should be noted that the specified constants a1, a2, a3, a4, o, p, k, and l are determined by performing the regression analysis on the plurality of sets of B, θ, and Y and the TEWL values and appropriate numerical values can be therefore determined in accordance with increase in the number of persons.

$B^o/Y^p$ and $Y^k/B^l$ in the equation 2 are examples of a second variable of the second embodiments. As described above the second variable is calculated from the first skin impedance value and the second skin impedance value.

In FIG. 7, a preferable positive correlation is shown measured using the CB value calculated based on the equation 2 and the TEWL value. In FIG. 7, a longitudinal axis indicates the CB value and a transverse axis indicates the TEWL value.

The operation processing apparatus 1301 can perform the regression analysis with many numerical values using not only θ but also B and Y. Thereby the specified constants a1, a2, a3, a4, o, p, k, and l can be determined so that CB value can have more correlation to preferable positive correlation to the TEWL value. Thus the operation processing apparatus in the second embodiment can calculate the CB value which have more preferable positive correlation with the TEWL value than the operation processing apparatus in the first embodiment.

Although 500 Hz and 100 kHz are used as the frequencies of the AC signal in the electronic equipment in the second embodiment, the frequency of the AC signal is not particularly limited. The application order of the AC signals is not particularly limited and whichever of them may be applied first.

The first skin impedance value in the operation processing apparatus 1301 in the second embodiment may be, for example, an admittance value, a conductance value, or the inverse values of the susceptance value, the admittance value, or the conductance value.

Alternatively, the first skin impedance value may be two or more values selected from the susceptance value, the admittance value and the conductance value, and the inverse values of the susceptance value, the admittance value, and the conductance value.

The second skin impedance value in the operation processing apparatus 1301 in the second embodiment may be, for example, the susceptance value, the conductance value, or the inverse values of the susceptance value, the admittance value, or the conductance value.

Alternatively, the second skin impedance value may be two or more values selected from the susceptance value, the admittance value, and the conductance value and the inverse values of the susceptance value, the admittance value, and the conductance value.

For example, with an admittance value based on the AC signal of 500 Hz (hereinafter, expressed as Y500) and the susceptance value based on the AC signal of 100 kHz (hereinafter, expressed as B100k), the CB value in the operation processing apparatus 1301 in the second embodiment may be calculated according to an equation in which Y and B in the equation 2 are respectively replaced with B100k and Y500.

For example with the B100k and B based on the AC signal of 500 Hz, the CB value may be calculated according to an equation in which Y in the equation 2 is replaced with B100k.

The calculation method of $\theta$ is not particularly limited in the operation processing apparatus 1301 in the second embodiment. With $\theta$ based on the delay time measured using the AC signal of 100 kHz and the detection signal (hereinafter, expressed as $\theta$100k,) the CB value may be calculated according to an equation in which $\theta$ in the equation 2 is replaced with $\theta$100k.

Furthermore, as described above, for example, $\theta=2\pi f\Delta t$, where $\Delta t$ is delay time measured using the AC signal and the detection signal and f is a frequency of the AC, can be satisfied ($2\pi$ and f are constants).

Therefore, $\theta$ in the equation 2 can be replaced with "$\Delta t$".

An operation processing apparatus according to a third embodiment of the invention will be described below.

The human skin is composed of epidermis with stratum corneum, dermis, and subcutaneous tissues. It is well known that the stratum corneum, which exists in the outermost side of the skin, largely contributes to a barrier function against an external environment.

It is also known that dermatitis or the like are developed when the stratum corneum is damaged suffering from such as decrease in the stratum corneum thickness, partial defect, or the like. Therefore it is said that the stratum corneum largely contributes to the maintenance of skin barrier function.

In view of this, the present inventors consider that a value representing the stratum corneum thickness is also significant as a value representing the skin barrier function as well as the TEWL value is. They have completed the operation processing apparatus in the third embodiment.

The operation processing apparatus in the third embodiment calculates a value representing the stratum corneum thickness with the similar equation in the operation processing apparatus in the first embodiment. The operation processing apparatus in the third embodiment has the same configuration of the operation processing apparatus 301 in the first embodiment and they are the same in view of the electronic equipment.

In the following description, the respective configurations of the skin barrier function measurement circuit including the operation processing apparatus in the third embodiment has the same reference numbers as are allocated to those of circuit in the first embodiment.

Referring to FIG. 3 and FIG. 8, operations of the skin barrier function measurement circuit in the third embodiment will be described. After the same operation in the first embodiment, the measurement starts.

First, the operation processing apparatus 301 outputs a control signal to cause the AC signal generation circuit 310 to generate an AC signal. The AC signal generation circuit 310 generates an AC signal using the control signal output by the operation processing unit 301. The AC signal generated is applied to the skin by the application electrode 201 (step S501).

The detection electrode 104 detects an AC signal passing through the skin and outputs the detection signal to the signal detection circuit 320. The signal detection circuit 320 converts the detection signal into an output signal. The output signal is output by the signal detection circuit 320 to the determination circuit 330 (step S502).

The determination circuit 330 determines whether the output signal falls within the range that the operation processing apparatus 301 can detect (step S503).

If the determination circuit 330 determines that the output signal does not fall within the range that the operation processing apparatus 301 can detect (NO at step S503), the operation processing apparatus 301 changes gain of the amplification circuit 321 in the signal detection circuit 320. Thereafter, the AC signal is applied to the skin by the application electrode 201 again (step S501) and the detection electrode 104 detects a detection signal passing through skin and outputs the detection signal to the signal detection circuit 320. The signal detection circuit 320 converts the detection signal into an output signal again (step S502). These processes are repeated until the output signal falls within the range that the operation processing apparatus 301 can detect.

If the determination circuit 330 determines that the output signal is a value in the detectable range (YES at step S503), the operation processing apparatus 301 calculates $\theta$ based on delay time measured using the AC signal and the detection signal. The calculated $\theta$ is stored in a storage medium in the operation processing apparatus 301 as a calculation result 1 (step S504).

The processor in the operation processing apparatus 301 calculates a numerical value representing a second skin barrier function (hereinafter, expressed as a SCT value) assigning $\theta$ stored as the calculation result 1 to the following equation 3 (step S505).

$$SCT = a \times \theta + \alpha \qquad [\text{Equation 3}]$$

In the equation, a and $\alpha$ are specified constants. The calculation method of the a and $\alpha$ is described later.

The display unit 102 displays the SCT value (step S506)

The calculation method of the a and $\alpha$ is described. The specified constants a and $\alpha$ are values that are appropriately defined by the regression analysis.

As described in the method above, $\theta$ is calculated with skins of a plurality of persons. A value representing the stratum corneum thickness is measured in the same part of the skin where $\theta$ is calculated with a confocal laser microscopy (Vivascope manufactured by Caliber Imaging & Diagnostics, Inc.).

The regression analysis is performed on a plurality of sets of $\theta$ and the values representing the stratum corneum thickness obtained in the measure described above to determine the specified constants a and $\alpha$ in the equation 3. These constants are determined so that $\theta$ can have a good correlation with stratum corneum thicknesses.

It should be noted that the measuring method of a value representing the stratum corneum thickness is not limited to the confocal laser microscopy, so another method may be used as long as it can measure a value representing the stratum corneum thickness.

As described in the method above, the operation processing apparatus in the third embodiment calculates SCT value based on the $\theta$ with the processor in the operation processing apparatus 301. The $\theta$ and the values representing the stratum corneum thickness are measured in a wide range of skin conditions from a normal condition skin to a rough condition skin. The equation is determined so that the $\theta$ can have a good correlation with the values representing the stratum corneum thickness. The SCT, one parameter of evaluation of the skin barrier function, is a numerical value accurately representing a skin barrier function in a wide range of skin conditions from a normal condition skin to a rough condition skin.

In the electronic equipment 1, the determination circuit 330 employs the method in which it determines the output signal and changes the gain of the amplification circuit 321 according to the result of the determination. The AC signal attenuates when it passes through skin. Amplifying too small AC signal leads to much noise, which lacks precision of the detection. On the other hand, too large AC signal falls outside a detectable range. Therefore making the detection signal gradually large with the determination circuit 330 enables the operation processing apparatus to receive an appropriate input signal. However, the method of detecting the output signal is not limited as long as it can accurately detect the output signal. For example, the determination circuit 330 may employ a method to modify a peak value of the AC signal to maintain the output signal, to which the detection signal is converted, within the detectable range even if the AC signal attenuates after passing through skin. Alternatively, the determination circuit 330 may employ a method to maintain, even if the AC signal attenuates after passing through skin, the output signal within the detectable range, modifying a resistance value of the detection signal to enlarge the peak value of the detection signal.

Furthermore, the AC signal generation circuit may be configured to generate one or more AC signals. If the AC signal generation circuit is configured to generate two or more AC signals, each θ based on the delay time measured using the respective AC signals and the respective detection signals detected based on the AC signals may be calculated. The respective SCT value may be calculated with the θ.

An operation processing apparatus according to a fourth embodiment of the invention will be described below.

The operation processing apparatus in the fourth embodiment calculates a value representing the stratum corneum thickness with the similar equation in the operation processing apparatus in the second embodiment. The operation processing apparatus in the fourth embodiment has the same configuration of the operation processing apparatus 1301 in the second embodiment and they are the same in view of electronic equipment.

In the following description, the respective configurations of the skin barrier function measurement circuit including the operation processing apparatus in the fourth embodiment has the same reference numbers as are allocated to those of circuit in the second embodiment.

Referring to FIG. 5 and FIG. 9, operations of the skin barrier function measurement circuit including the operation processing apparatus in the fourth embodiment will be described. After the same operation in the first embodiment, the measurement starts.

First, the operation processing apparatus 1301 outputs a control signal to cause the AC signal generation circuit 1310 to generate an AC signal of 500 Hz. The AC signal generation circuit 1310 generates an AC signal of 500 Hz using the control signal output by the operation processing unit 1301. The AC signal of 500 Hz is applied to skin by the application electrode 201 (step S1501).

The detection electrode 104 detects an AC signal passing through the skin and outputs the detection signal to the signal detection circuit 320. The signal detection circuit 320 converts the detection signal into an output signal.

The output signal is output by the signal detection circuit 320 to the determination circuit 330 (step S1502).

The determination circuit 330 determines whether the output signal falls within the range that the operation processing apparatus 1301 can detect (step S1503).

If the determination circuit 330 determines that the output signal does not fall within the range that the operation processing apparatus 1301 (NO at step S1503), the operation processing apparatus 1301 changes gain of the amplification circuit 321 in the signal detection circuit 320. Thereafter, the AC signal of 500 Hz is applied to the skin by the application electrode 201 again (step S1501) and the detection electrode 104 detects a detection signal passing through skin and outputs the detection signal to the signal detection circuit 320. The signal detection circuit 320 converts the detection signal into an output signal again (step S1502).These processes are repeated until the output signal falls within the range that the operation processing apparatus 1301 can detect.

If the determination circuit 330 determines that the output signal is a value in the detectable range (YES at step S1503), the operation processing apparatus 1301 calculates θ based on delay time measured using the AC signal of 500 Hz and the detection signal. In addition, the operation processing apparatus 1301 calculates B based on the θ and a peak value of the detection signal. The calculated θ and B are stored as a calculation result 1 in a storage medium in the operation processing apparatus 1301 (step S1504).

Subsequently, the operation processing apparatus 1301 outputs a control signal to cause the AC signal generation circuit 1310 to generate an AC signal of 100 kHz. The AC signal generation circuit 1310 generates an AC signal of 100 kHz using the control signal output by the operation processing unit 1301. The AC signal of 100 kHz is applied to the skin by the application electrode 201 (step S1505).

The detection electrode 104 detects an AC signal passing through the skin and outputs the detection signal to the signal detection circuit 320.The signal detection circuit 320 converts the detection signal into an output signal. The output signal is output by the signal detection circuit 320 to the determination circuit 330 (step S1506).

The determination circuit 330 determines whether the output signal falls within the range that the operation processing apparatus 1301 can detect (step S1507).

If the determination circuit 330 determines that the output signal does not fall within the range that the operation processing apparatus 1301 can detect (NO at step S1507), the operation processing apparatus 1301 changes gain of the amplification circuit 321 in the signal detection circuit 320. Thereafter, the AC signal of 100 Hz is applied to the skin by the application electrode 201 again (step S1505) and the detection electrode 104 detects a detection signal passing through skin and outputs the detection signal to the signal detection circuit 320. The signal detection circuit 320 converts the detection signal into an output signal again (step S1506). These processes are repeated until the output signal falls within the range that the operation processing apparatus 1301 can detect.

If the determination circuit 330 determines that the output signal is a value in the detectable range (YES at step S1507), the operation processing apparatus 1301 calculates an admittance value (hereinafter, also expressed as Y) based on delay time measured using the AC signal of 100 kHz and the detection signal and a peak value of the detection signal. The Y is an example of a second skin impedance of the second embodiments. The calculated Y is stored as a calculation result 2 in the storage medium in the operation processing apparatus 1301 (step S1508).

The processor in the operation processing apparatus 1301 calculates a numerical value representing a second skin barrier function (SCT value) assigning B and θ stored as the calculation result 1 and Y stored as the calculation result 2 to the following equation 4 (step S1509).

$$SCT = a1 \times B^o/Y^p + a2 \times \theta + a3 \times Y^k/B^l + a4 \qquad [\text{Equation 4}]$$

In the equation, a1, a2, a3, a4, o, p, k, and l are specified constants. The calculation method of the a1, a2, a3, a4, o, p, k, and l is described later.

The display unit 102 displays the SCT value calculated based on the equation 4 (step S1510)

The calculation method of the a1, a2, a3, a4, o, p, k, and l is described. The specified constants a1, a2, a3, a4, o, p, k, and l are values that are appropriately defined by the regression analysis.

As described in the method above, B, θ, and Y are calculated with skins of a plurality of persons. A value representing the stratum corneum thickness is measured in the same part of the skin where B, θ, and Y is calculated with a d confocal laser microscopy (Vivascope manufactured by Caliber Imaging & Diagnostics, Inc.).

The regression analysis is performed on a plurality of sets of B, θ, and Y and the values representing the stratum corneum thickness obtained in the measure described above to determine the specified constants a1, a2, a3, a4, o, p, k, and l in the equation 4. These constants are determined so that B, θ, and Y can have the good correlation with the values representing the stratum corneum thickness.

For example, numerical values of "−312.2" as a1, "0.1483" as a2, "−0.01" as a3, "5.1574" as a4, "0.5" as o, "0.25" as p, "0.25" as k, and "0.5" as l are obtained. These values are mere examples of appropriate values. It should be noted that the specified constants a1, a2, a3, a4, o, p, k, and l are determined by performing the regression analysis on the plurality of sets of B, θ, and Y and the values representing the stratum corneum thickness and appropriate numerical values can be therefore determined in accordance with increase in the number of persons.

It should be noted that the measuring method of a value representing the stratum corneum thickness is not limited to the confocal laser microscopy and a well-known method may be appropriately used.

$B^o/Y^p$ and $Y^k/B^l$ in the equation 4 are examples of a second variable of the forth embodiments. As described above the second variable is calculated from the first skin impedance value and the second skin impedance value.

FIG. 10 a preferable positive correlation is shown measured using the SCT value calculated based on the equation 4 and the values representing the stratum corneum thickness. In FIG. 10, a longitudinal axis indicates the SCT value and a transverse axis indicates a measured value of the value representing the stratum corneum thickness by the confocal laser microscopy.

In FIG. 10, a preferable positive correlation is showed measured using the SCT value calculated based on the equation 4 and the values representing the stratum corneum thickness.

If the SCT value is negative due to the property of the confocal laser microscopy, it is preferable that the operation processing apparatus 1301 convert the SCT value to "0". The processing method is not particularly limited and a known method can be used.

The operation processing apparatus 1301 can perform the regression analysis with many numerical values using not only θ but also B and Y. Thereby the specified constants a1, a2, a3, a4, o, p, k, and l can be determined so that SCT value can have more correlation to preferable positive correlation to the value representing the stratum corneum thickness. Thus the operation processing apparatus in the fourth embodiment can calculate the SCT value which have more preferable positive correlation with the numerical value representing the stratum corneum thickness than the operation processing apparatus in the third embodiment.

Although 500 Hz and 100 kHz are used as the frequencies of the AC signal in the electronic equipment in the fourth embodiment, the frequency of the AC signal is not particularly limited. The application order of the AC signals is not particularly limited and whichever of them may be applied first.

The first skin impedance value in the operation processing apparatus 1301 in the fourth embodiment may be, for example, an admittance value, a conductance value, or the inverse values of the susceptance value, the admittance value, or the conductance value.

Alternatively, the first skin impedance value may be two or more values selected from the susceptance value, the admittance value and the conductance value, and the inverse values of the susceptance value, the admittance value, and the conductance value.

The second skin impedance value in the operation processing apparatus 1301 in the fourth embodiment may be, for example, the susceptance value, the conductance value, or the inverse values of the susceptance value, the admittance value, or the conductance value.

Alternatively, the second skin impedance value may be two or more values selected from the susceptance value, the admittance value, and the conductance value, and the inverse values of the susceptance value, the admittance value, and the conductance value.

For example, with an admittance value based on the AC signal of 500 Hz (hereinafter, expressed as Y500) and the susceptance value based on the AC signal of 100 kHz (hereinafter, expressed as B100k), the SCT value in the operation processing apparatus 1301 in the fourth embodiment may be calculated according to an equation in which Y and B in the equation 2 are respectively replaced with B100k and Y500.

For example with the B100k and B based on the AC signal of 500 Hz, the SCT value may be calculated according to an equation in which Y in the equation 4 is replaced with B100k.

The calculation method of θ is not particularly limited in the operation processing apparatus 1301 in the fourth embodiment. With θ based on the delay time measured using the AC signal of 100 kHz and the detection signal (hereinafter, expressed as θ100k,) the SCT value may be calculated according to an equation in which θ in the equation 4 is replaced with θ100k.

The program in the invention is a computer readable program to make a computer execute the function of the operation processing apparatus function of the present invention. The program is an operation program that collaborates with a computer. The program is stored in a non-transitory computer readable storage medium.

In addition, the present invention also relates to an evaluation method of the skin barrier function. This evaluation method includes an operation process of evaluating a skin barrier function using a variable based on delay time measured using an AC signal generated by an AC signal generation circuit and a detected signal by the detection electrode after passing through the skin. Moreover, the evaluation method may include an application process of applying the AC signal to skin, a measurement process of measuring the signal passing through the skin and converting it into an output signal, and a display process of displaying a numerical value (CB value or SCT value) representing the skin barrier function calculated in the operation process.

The operation process may include a calculation process of calculating the CB value or the SCT value with θ calculated based on the delay time measured using the AC signal generated by the AC signal generation circuit and the signal passed through the skin by the application electrode as in the operation method in the operation processing apparatus 301. Specifically the CB value or the SCT value may be calculated based on the equation 1 or the equation 3.

Alternatively, the operation process may include a calculation process of calculating the CB value or the SCT value with the θ and the skin impedance values calculated based on the delay time and the peak value of the detection signal in a similar way as in the operation method in the operation processing apparatus 1301. Specifically the CB value or the SCT value may be calculated based on the equation 2 or the equation 4.

Furthermore, as described above, for example, $\theta=2\pi f\Delta t$, where $\Delta t$ is delay time measured using the AC signal and the detection signal and f is a frequency of the AC, can be satisfied ($2\pi$ and f are constants).

Therefore, θ in the equation 4 can be replaced with "$\Delta t$".

With the operation processing, the evaluation method according to the invention can accurately calculate the skin barrier function in a wide range of skin conditions from a normal condition to a rough skin condition, which a stratum corneum is totally exfoliated, or the like.

1 Electronic equipment
101 Main body portion
102 Display unit
103 Probe
104 Detection electrode
201 Application electrode
202 Ground electrode
340 Ground terminal
301 and 1301 Operation processing apparatus
310 and 1310 AC signal generation circuit
320 Signal detection circuit
321 Amplification circuit
322 Filter circuit
323 Current detection circuit
324 Detection resistance
330 Determination circuit
351, 1351, 1352, 1353, and 1316 Output terminal
1311 500 Hz-AC signal generation circuit
1312 100 kHz-AC signal generation circuit
1313 Switching circuit
361, 362, 1314, and 1315 Input terminal

The invention claimed is:
1. A method of evaluating a skin barrier function by an electronic equipment, the method comprising the steps of:
generating a first alternating-current (AC) signal in a first frequency by an alternating-current (AC) signal generation circuit;
applying the first AC signal by an application electrode and making the first AC signal pass through skin;
detecting the first AC signal passed through the skin by a detection electrode;
converting the first AC signal to a first output signal and outputting the first output signal by a signal detection circuit;
determining whether the first output signal falls within a detectable range, and when the first output signal is not within the detectable range, repeating the steps of generating, applying, and detecting the first AC signal and the steps of converting and outputting the first output signal until the first output signal falls within the detectable range;
calculating a variable by a processor of an operation processing apparatus based on delay time measured using the first AC signal generated by the AC signal generation circuit and the first AC signal applied by the application electrode and passed through the skin;
storing a calculation result of the variable calculated by the processor;
calculating a first skin impedance value, which is a susceptance value, based on the first AC signal generated by the AC signal generation circuit;
storing a calculation result of the first skin impedance value calculated by the processor;
generating a second alternating-current (AC) signal in a second frequency, which is different from the first frequency, by the alternating-current (AC) signal generation circuit;
applying the second AC signal by an application electrode and making the second AC signal generated pass through skin;
detecting the second AC signal passed through the skin by a detection electrode;
converting the second AC signal to a second output signal and outputting the second output signal by the signal detection circuit;
determining whether the second output signal falls within a detectable range, and when the second output signal is not within the detectable range, repeating the steps of generating, applying, and detecting the second AC signal and the steps of converting and outputting the second output signal until the second output signal falls within the detectable range;
calculating a second skin impedance value, which is an admittance value, based on the second AC signal generated by the AC signal generation circuit;
storing a calculation result of the second skin impedance value calculated by the processor;
calculating a numerical value representing a skin barrier function by the processor based on the variable, the calculation result of the first skin impedance value, and the calculation result of the second skin impedance value;
wherein the step of calculating the numerical value representing the skin barrier function includes using Equation 1,

$$CB = a1 \times B^o/Y^p + a2 \times \theta + a3 \times Y^k/B^l + a4 \qquad \text{[Equation 1]}$$

wherein CB is the numerical value representing the skin barrier function,
B is the susceptance value,
Y is the admittance value,
θ is the variable, and
a1, a2, a3, a4, o, p, k, and l are constants, and
wherein the constants of a1, a2, a3, a4, o, p, k, and l in Equation 1 are determined by performing, on the processor, a regression analysis of a plurality of sets of B, θ, and Y and Trans Epidermal Water Losses (TEWL) values.

2. A method of evaluating a skin barrier function by an electronic equipment, the method comprising the steps of:

generating a first alternating-current (AC) signal in a first frequency by an alternating-current (AC) signal generation circuit;

applying the first AC signal by an application electrode and making the first AC signal generated pass through skin;

detecting the first AC signal passed through the skin by a detection electrode;

converting the first AC signal to a first output signal and outputting the first output signal by a signal detection circuit;

determining whether the first output signal falls within a detectable range, and when the first output signal is not within the detectable range, repeating the steps of generating, applying, and detecting the first AC signal and the steps of converting and outputting the first output signal until the first output signal falls within the detectable range;

calculating a variable by a processor of an operation processing apparatus based on delay time measured using the first AC signal generated by the AC signal generation circuit and the first AC signal applied by the application electrode and the passed through the skin;

storing a calculation result of the variable calculated by the processor;

calculating a first skin impedance value, which is a susceptance value, based on the first AC signal generated by the AC signal generation circuit;

storing a calculation result of the first skin impedance value calculated by the processor;

generating a second alternating-current (AC) signal in a second frequency, which is different from the first frequency, by the alternating-current (AC) signal generation circuit;

applying the second AC signal by an application electrode and making the second AC signal generated pass through skin;

detecting the second AC signal passed through the skin by a detection electrode;

converting the second AC signal to a second output signal and outputting the second output signal by the signal detection circuit;

determining whether the second output signal falls within a detectable range, and when the second output signal is not within the detectable range, repeating the steps of generating, applying, and detecting the second AC signal and the steps of converting and outputting the second output signal until the second output signal falls within the detectable range;

calculating a second skin impedance value, which is an admittance value, based on the second AC signal generated by the AC signal generation circuit;

storing a calculation result of the second skin impedance value calculated by the processor;

calculating a numerical value representing a skin barrier function by the processor based on the variable, the calculation result of the first skin impedance value, and the calculation result of the second skin impedance value;

wherein the step of calculating the numerical value representing the skin barrier function includes using Equation 2, $$SCT = a1 \times B^o / Y^p + a2 \times \theta + a3 \times Y^k / B^l + a4 \qquad \text{[Equation 2]}$$

wherein SCT is the numerical value representing the skin barrier function,

B is the susceptance value,

Y is the admittance value,

θ is the variable, and a1, a2, a3, a4, o, p, k, and l are constants; and wherein the constants of a1, a2, a3, a4, o, p, k, and l in Equation 2 are determined by performing, on the processor, a regression analysis of a plurality of sets of B, θ and Y and values representing a stratum corneum thickness.

* * * * *